(12) United States Patent  
Doepker

(10) Patent No.: US 8,006,364 B2
(45) Date of Patent: Aug. 30, 2011

(54) METHOD AND APPARATUS FOR REMOVING WORKPIECES FROM THE BOTTOM OF A STACK OF WORKPIECES

(75) Inventor: Brian T. Doepker, Kalida, OH (US)

(73) Assignee: The Schnipke Family, LLC, Ottoville, OH (US)

( * ) Notice: Subject to any disclaimer, the term of this patent is extended or adjusted under 35 U.S.C. 154(b) by 561 days.

(21) Appl. No.: 12/118,686

(22) Filed: May 10, 2008

(65) Prior Publication Data

US 2009/0279997 A1 Nov. 12, 2009

(51) Int. Cl.
*B23P 19/00* (2006.01)
*B23Q 7/00* (2006.01)
(52) U.S. Cl. ............................ 29/426.1; 29/559; 29/284
(58) Field of Classification Search .................. 29/426.1, 29/426.3, 426.5, 559, 284, 809; 59/71; 227/175.1, 227/176.1
See application file for complete search history.

(56) References Cited

U.S. PATENT DOCUMENTS

| | | |
|---|---|---|
| 5,653,928 A | 8/1997 | Schnipke |
| 5,836,147 A | 11/1998 | Schnipke |
| 6,047,466 A * | 4/2000 | Karpman et al. ............... 29/809 |
| 6,158,205 A | 12/2000 | Schnipke et al. |
| 6,729,119 B2 | 5/2004 | Schnipke et al. |
| 7,207,168 B2 | 4/2007 | Doepker et al. |

* cited by examiner

*Primary Examiner* — Jermie Cozart
(74) *Attorney, Agent, or Firm* — Jason H. Foster; Kremblas & Foster

(57) ABSTRACT

A method and apparatus for removing the lowest workpiece from a stack of a plurality of substantially similar workpieces. A horizontal shuttle has a lip on its edge, and is driven in one direction to remove the lip from a void beneath the stack, thereby permitting the stack to fall. The lowest workpiece drops into the void, and the next higher workpiece rests on the upper surface of the shuttle lip. The shuttle is subsequently reversed to drive the workpiece into a slot in a vertical clamp body. The clamp body is driven downwardly, thereby driving the workpiece downwardly, to be acted upon by a secondary device, such as a conventional degating apparatus.

8 Claims, 17 Drawing Sheets

METHOD AND APPARATUS FOR REMOVING WORKPIECES FROM THE BOTTOM OF A STACK OF WORKPIECES

BACKGROUND OF THE INVENTION

1. Field of the Invention

This invention relates generally to devices for removing component parts from a stack and using them in the assembly of an article of manufacture, and more particularly relates to a method and apparatus for removing component parts from the bottom of a stack of parts to permit supplying of the stack from the top.

2. Description of the Related Art

In the field of microsurgery, a surgical instrument having a cutting blade traverses a specific path through tissue. One feature of the surgical instrument is a single-use cartridge that is a holder for surgical staples. The cartridge is an elongated plastic body with a longitudinal channel that serves as a guide for a surgical blade. The cartridge has rows of small staples on opposite sides of the channel, and these rows are aligned parallel to the guide channel. Drivers are inserted in apertures (also called "pockets") aligned with the rows in order to push the staples out of the cartridge and through the adjacent tissue. Before the blade has made its cut, each side of the incision is stapled together by displacing the drivers relative to the cartridge. This displacement forces the staples against an anvil on the opposing side of the surgical instrument as the cartridge and the anvil deflect the points of the staples into a clasping position.

There may be as many as fifty or more very small staples on each side of a two-inch incision. Each staple can be driven into the tissue to close the incision by the correspondingly small drivers. The task of inserting the drivers into the cartridge is labor-intensive due to the small size and number of the drivers and the apertures.

One prior art system for mounting the staple drivers into apertures in the cartridge includes a plastic holder, commonly referred to as a "tree" having aligned "branches" with drivers integrally formed on an end of each of the aligned branches. The conventional cartridge is placed in an apparatus and the tree with drivers is hand-manipulated to place the drivers adjacent the entrance to the pockets. This is normally accomplished by inserting the drivers in funnel-shaped passages that are aligned with the pockets. Each driver is subsequently driven into the associated pocket of the cartridge. The separation of the individual drivers from the branch of the tree on which it is mounted is accomplished by flexing the branches of the tree manually to break the tree away from the staple drivers. Then, a hand-manipulated tool is used to press each staple driver down into the cartridge to near the pocket opening on the opposite side of the cartridge.

The finger operation of pressing each driver into a pocket, the flexing of the branches and the subsequent pressing from the hand-operated prongs can misalign some of the drivers within the pockets. Furthermore, the sizes of the pockets and the drivers vary slightly due to the minute structure involved and the fact that both the cartridge and the staple drivers are formed of thermoplastic resin, which does not always result in a perfectly formed structure. This combination of factors can cause some "play" in the assembly, which can result in an alignment problem. In particular, inversion of the cartridge after assembly can result in some of the drivers being displaced from their pockets. If a staple driver is absent, no staple will be driven into the tissue at that point in the incision.

Another problem is the imprecision in the process of separating the staple drivers from the branches of the plastic "tree", a process referred to as "degating." The drivers are mounted to the tree prior to insertion in the cartridge, but must be removed from the tree before or during the insertion process. Because the separation of a driver from the tree is not precise, it leaves some material on one side of each driver. The remnants of material left on the drivers is not a predictable size, and often the remnants are larger than desired. While it is not practical to remove all of the holder material from the side of each driver in the separation process, it is important that the amount of material left on each driver be relatively consistent between drivers. This is because the material left on the side tends to cause friction when the staple driver is used in surgery. If the amount of material left is consistent, it allows a user of such a staple cartridge to accurately predict the amount of force needed to expel a staple in surgery. In addition, the smaller the volume of material left, the less friction will be generated, and the less the force required to use the staple cartridge.

It is known in the prior art to insert drivers mechanically into surgical stapling cartridges, as shown in U.S. Pat. No. 5,836,147 to Schnipke, U.S. Pat. No. 5,653,928 to Schnipke, U.S. Pat. No. 6,158,205 to Schnipke et al., and U.S. Pat. No. 7,207,168 to Doepker et al., all of which are incorporated herein by reference. Workers manually position the cartridges, as well as the holders that contain the drivers and hold them relative to the machine, in the machines disclosed in these patents, and then actuate the machine to insert the tiny drivers into the pockets in the cartridges. After a fraction of the total number of drivers is inserted by one machine, the cartridge is then manually transported to the next machine, which inserts another fraction of the drivers. In U.S. Pat. No. 6,729,119 to Schnipke et al., which is incorporated herein by reference, a robotic loader is described for use in filling the cartridges discussed herein with the use of fewer workers than the prior art.

The machines disclosed in the patents referenced above, although representing a significant improvement over the prior art, still require parts to be fed in batches to the machines. This requires periods of time in which the machine is not operating in order to supply components to the machines. Thus, there is a need for an apparatus that permits continuous feeding of component parts to the above machines, and to other machines that are unrelated to the above.

BRIEF SUMMARY OF THE INVENTION

The apparatus and method described herein allow the advantageous ejection of the lowest part or parts from a stack of similar and preferably identical parts. Such a system permits a stack of parts to be continuously filled from above and held in place by the force of gravity. When the stack of parts needs to be refilled, due to falling below a predetermined height, a sensor signals a computer and the computer actuates a robot to refill the stack. Thus, a continuous process, which operates uninterrupted, is realized from the invention. The preferred apparatus includes a plate to which a pair of rigid buffer columns are mounted with grooves inwardly facing one another. Protruding tabs on a part, such as a "tree" that is used to transport drivers to a degating apparatus that inserts the drivers in a surgical cartridge, extend into the grooves for restricting the lateral and longitudinal movement of the trees. A shuttle is slidably mounted to the plate substantially parallel to the plane of the plate. The shuttle has an upper surface that supports the stack of trees, but is withdrawn from beneath the grooves to permit one of the trees to fall downwardly into a slot between the column and the plate. The shuttle then reverses and drives the tree into a slot on a vertically moveable shuttle, such as a clamp body. The clamp body is driven in a path that is transverse, and preferably substantially perpendicular, to the path of the shuttle, although this is not required. This drives the tree downwardly toward a degating machine or other device that acts upon the trees.

A clamp bar accompanies the clamp bodies and the tree, and applies a clamping force to the tree while its drivers are being inserted into the cartridge. When the drivers are severed from the tree, the cutting force causes the scrap (i.e., all parts of the tree other than the drivers) to rapidly move away from the degating apparatus. Because the slot into which the protruding tabs on the tree are inserted opens toward the shuttle that drives it thereinto, the opening of the slot faces away from the degating apparatus. Therefore, the rapid movement of the scrap caused by cutting the drivers from the tree causes the scrap to move rapidly out of the slots and toward a scrap collection area. This can be further encouraged by a blast of air or other mechanism.

The slots on the clamp bodies that accept the tree's tabs are displaced as far below the plate at the time the drivers are cut from the tree as is necessary to permit this movement of the scrap away from the degating apparatus.

Figure 1:
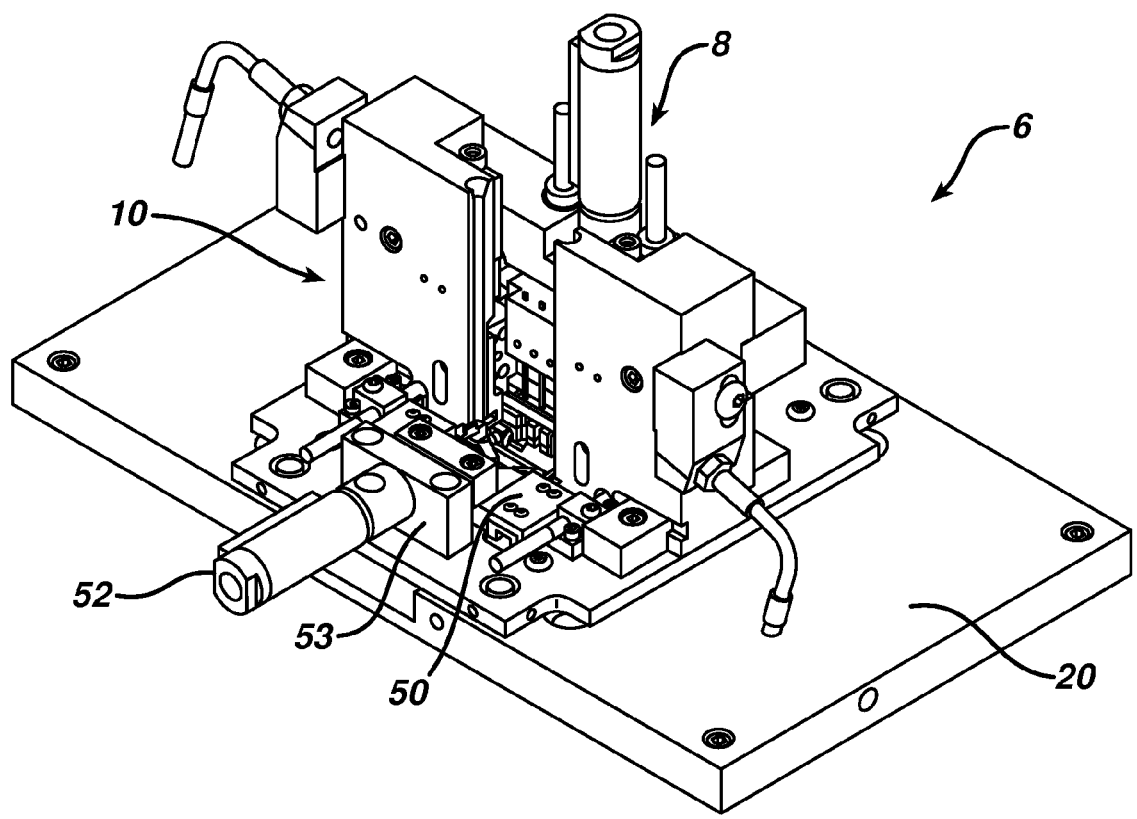
FIG. 1 is a view in perspective illustrating a preferred embodiment of the present invention in a cooperating configuration with a degating apparatus.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or term similar thereto are often used. They are not limited to direct connection, but include connection through other elements where such connection is recognized as being equivalent by those skilled in the art.

DETAILED DESCRIPTION OF THE INVENTION

The apparatus 6 shown in FIG. 1 is the stack feeding apparatus 10 of the invention mounted in cooperation with a conventional degating apparatus 8, with which the apparatus 10 is designed to cooperate. The combination of the apparatus 10 and the degating apparatus 8 is exploded in FIG. 2 to provide viewing of details of the configuration. It will be apparent from the description herein that both apparatuses are mounted to a base 20 having a central aperture 22 into which a conventional surgical cartridge (not shown) is disposed during operation. This base is preferably mounted in an assembly operation in which pallets, or other moveable objects, are conveyed along from station to station to have component parts mounted in a surgical cartridge, as is conventionally known.

In the preferred operation, "trees" with drivers are placed in the apparatus 10, and the apparatus 10 mechanically inserts the trees into the degating apparatus 8. The degating apparatus 8 separates the drivers from the "branches", inserts the drivers into the apertures or "pockets" of a conventional surgical cartridge in a conventional manner, and the scrap material is ejected out of the apparatus 6. The driver insertion and degating process is described in detail in the patents incorporated by reference herein.

Figure 3:
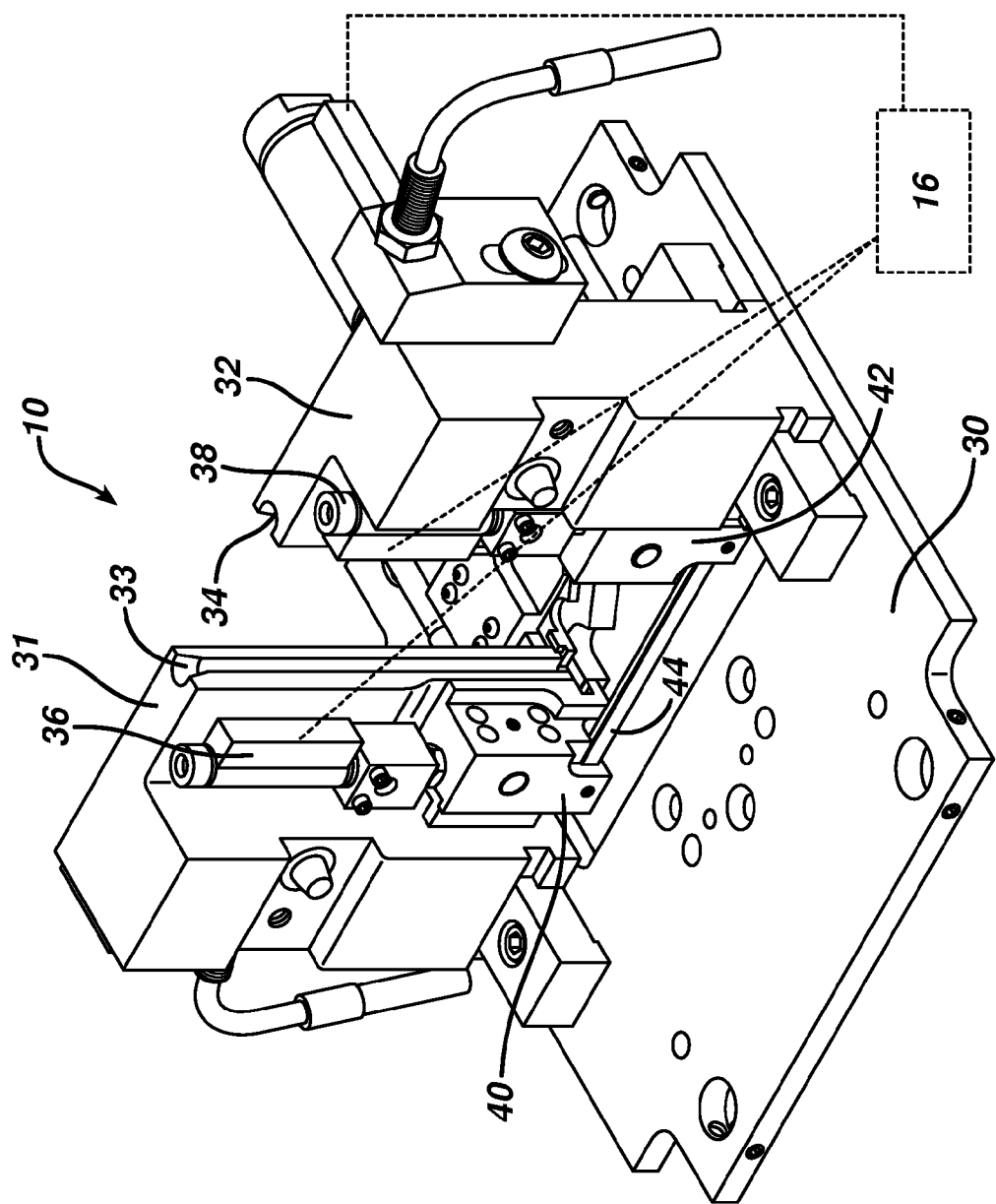
FIG. 3 is a view in perspective illustrating a preferred embodiment of the present invention.

The novel aspects of the apparatus 10 are described in detail herein, with reference to the figures, beginning with FIG. 3, which shows the apparatus 10 with the degating apparatus 8 removed. The apparatus 10 is not found in this state during normal operation, but the apparatus 10 is illustrated in this manner for clarity. The plate 30 is mounted rigidly to the base 20, as shown in FIG. 1, and has a central aperture 35 that corresponds with the central aperture 22 of the plate 20. As noted above, a cartridge mounted in a pallet is raised into precise registration with these apertures 22 and 32, so that the drivers can be inserted in the cartridge thereof.

A pair of upright buffer columns 31 and 32 rigidly mount to the plate 30 with facing grooves 33 and 34, respectively, that receive trees as described below and form a guide channel for the trees. Most preferably, protruding tabs (not visible) extend laterally from the trees and are inserted in the grooves 33 and 34, thereby securing the trees from longitudinal movement and lateral movement except as described herein.

Figure 2:
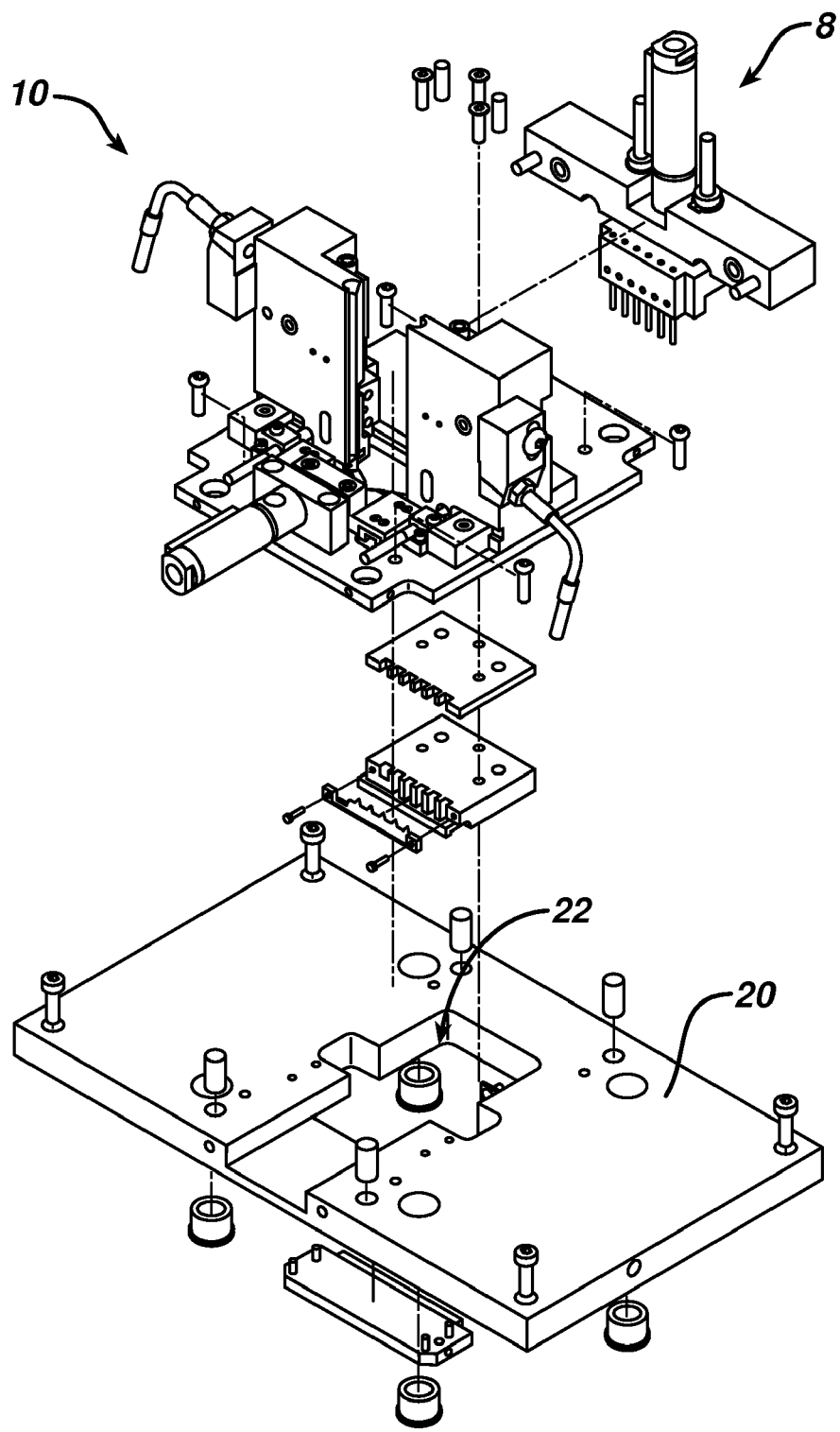
FIG. 2 is an exploded view illustrating the embodiment of FIG. 1.

It should be noted that terms such as "front," "rear," "top," "bottom," "horizontally," "vertically," "above" and "below" are used herein to describe the relative position and orientation of various components of the invention, all with respect to the geometry and orientation of the apparatus 10 in an operable orientation, which is shown in FIGS. 1 and 2. Likewise, the terms "laterally," "longitudinally," "upstream" and "downstream" relate to the direction of travel of trees during their movement into and out of the degating apparatus 8, in which the longitudinal direction refers to the direction the trees move when first driven out of the grooves 33 and 34, and the upstream position is a point from which a tree moving along the longitudinal axis starts and the downstream position is a point to which the tree on moves from the upstream position. This terminology includes the words specifically mentioned, derivatives thereof, and words of similar import, as understood by a person having ordinary skill in the art.

Figure 4:
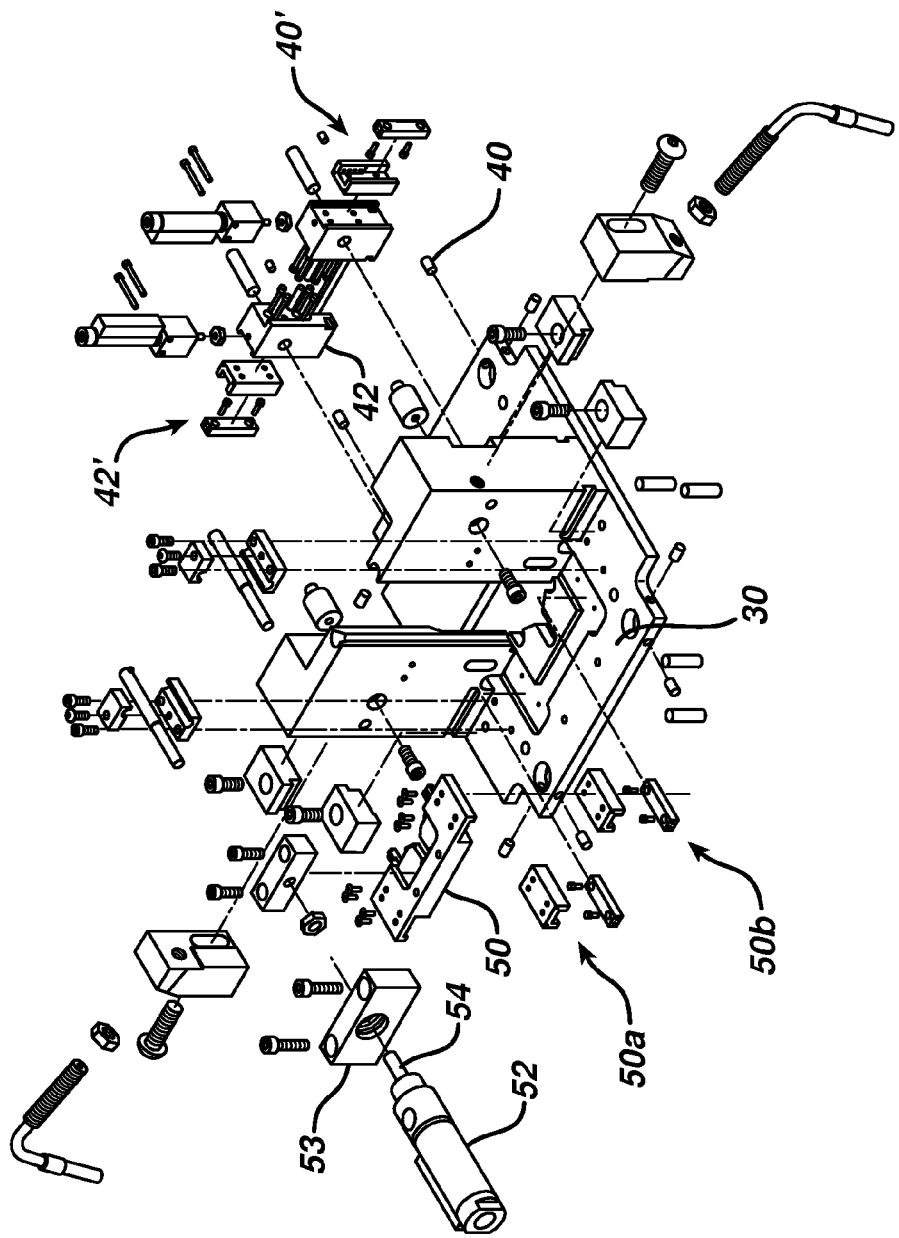
FIG. 4 is an exploded view illustrating the embodiment of FIG. 3.

Two prime movers, such as the conventional pneumatic rams 36 and 38, are mounted to the buffer columns 31 and 32, and are drivingly linked, such as by their drive rods (not visible) to the vertical clamp bodies 40 and 42. The rams 36 and 38 are connected to the central computer 16, which is preferably a programmable logic controller (PLC) or equivalent multifunction programmable computer. The clamp bodies 40 and 42 are slidably mounted to the buffer columns 31 and 32, such as by the roller slide assemblies 40' and 42' or equivalent, respectively, which are illustrated in FIG. 4. The clamp bodies 40 and 42 are driven along a substantially vertical, linear path relative to the buffer columns 31 and 32. A clamp bar 44 is rigidly mounted to each of the clamp bodies 40 and 42, and moves with the same as described in more detail below.

Referring to FIGS. 1 and 4, the horizontal shuttle 50 is slidably mounted to the plate 30, such as by roller slide assemblies 50a and 50b or equivalent, which are preferably substantially identical to the roller slide assemblies 40' and 42'. A prime mover, preferably the conventional pneumatic ram 52, is mounted to the member 53, which is rigidly attached to the plate 30, with its drive rod 54 extending slidably therethrough for attachment to the shuttle 50, or to other members rigidly attached to the shuttle 50. The ram 52 is connected to the central computer 16. The ram 52 and the rams 36 and 38 are controlled by the central computer 16, and are actuated thereby in a conventional manner. The shuttle 50 is driven along a path substantially parallel to the plane of the plate 30 toward and away from the central aperture 22, and the clamp bodies 40 and 42 are driven substantially vertically within the central aperture 22. It is possible for the shuttle to be oriented other than horizontally, and the clamp bodies 40 and 42 to be oriented other than vertically, but because the force due to gravity biases the components when they are in the preferred configuration, mechanical biases would be necessary to compensate for this modification.

Figure 5:
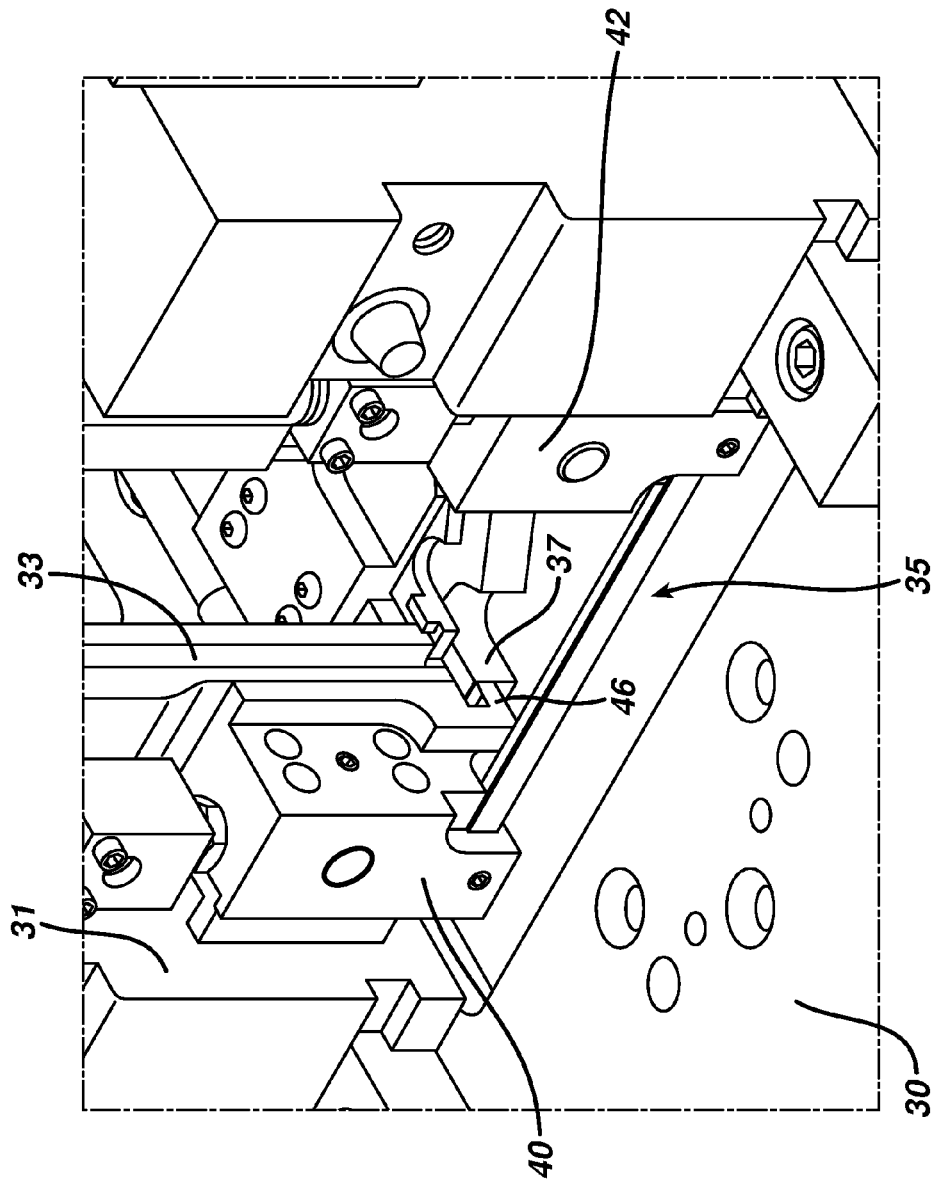
FIG. 5 is a magnified view of a portion of the embodiment of FIG. 3.
Figure 6:
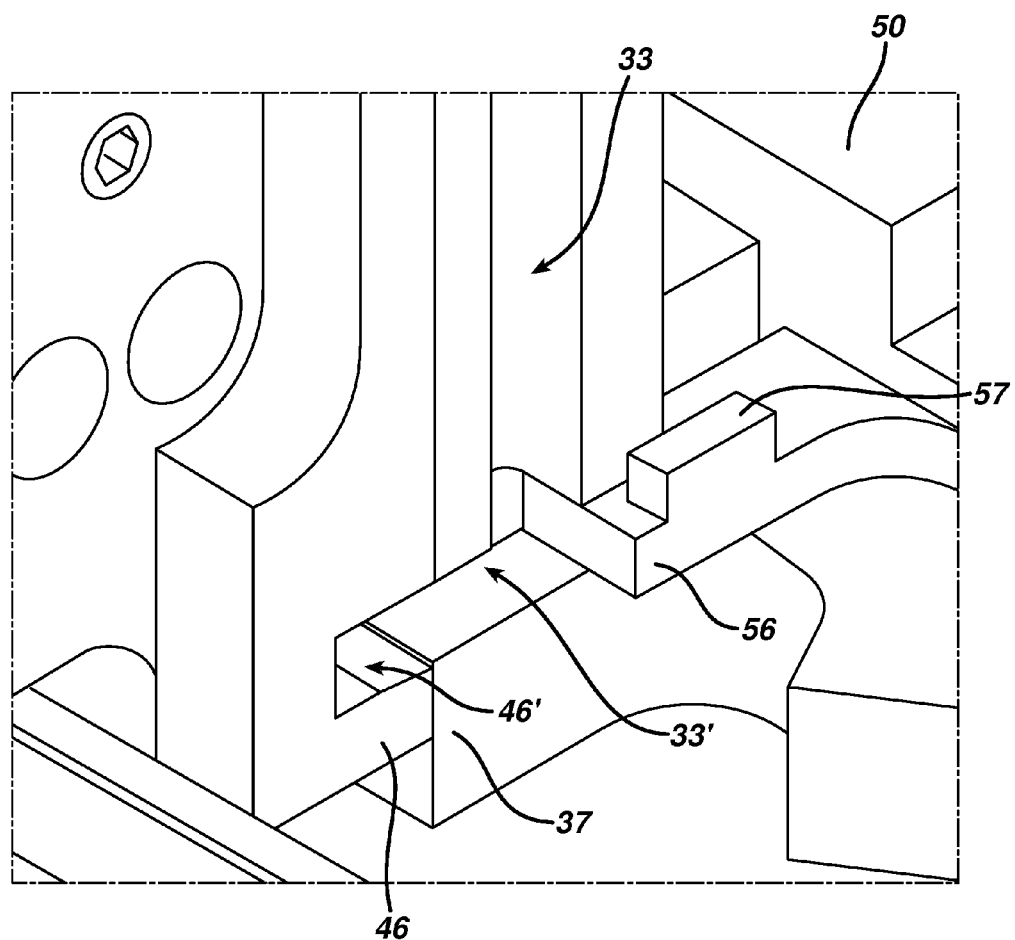
FIG. 6 is a further magnified view of a portion of the embodiment of FIG. 3.
Figure 7:
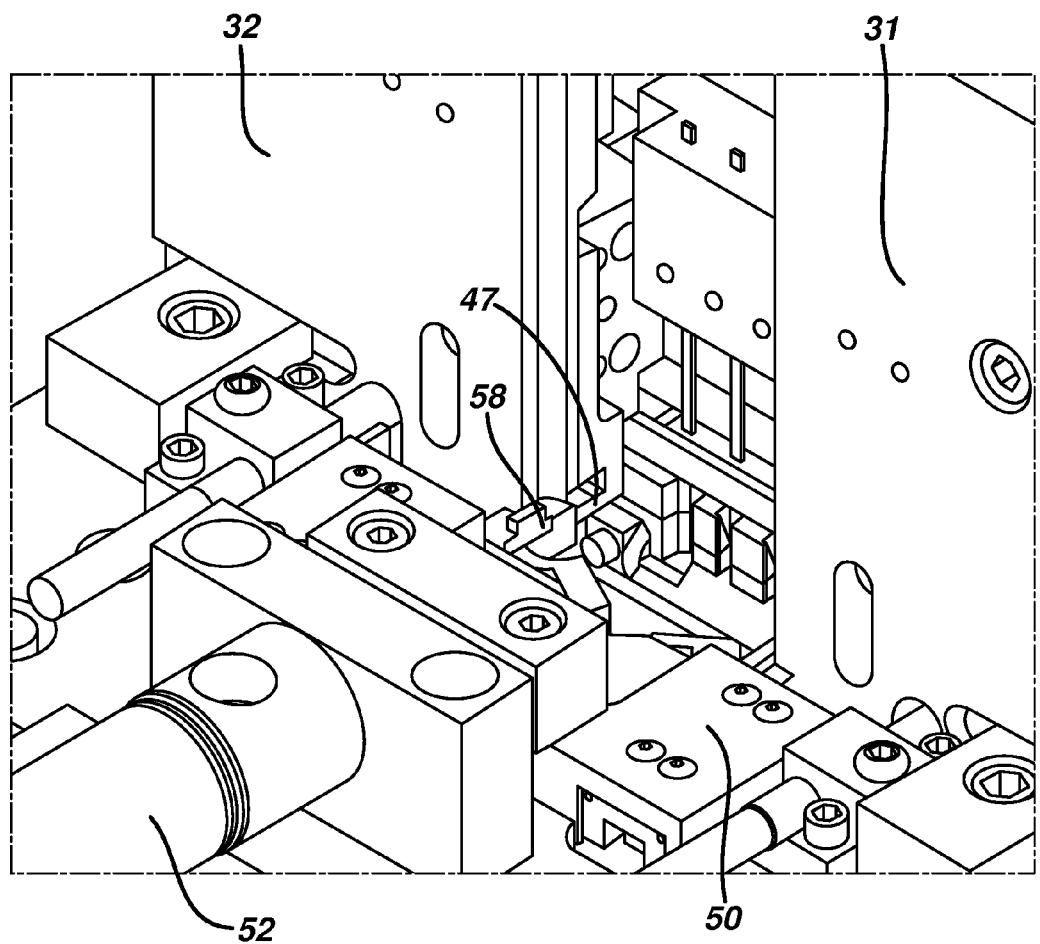
FIG. 7 is a view in perspective illustrating the embodiment of FIG. 1 in a first step of a preferred process.

Referring to FIG. 5, which is a magnified view of an area adjacent the central aperture 37 of FIG. 3, the clamp bodies 40 and 42 are shown having lower lips 46 and 47 (the lip 47 is visible in FIG. 7). The lip 46 is adjacent a shoulder 37 of the plate 30, and there is a mirror image shoulder (not visible) adjacent the lip 47. As the clamp body 40 moves vertically, the lip 46 moves relative to, and adjacent, the shoulder 37. The slot 46', shown in more detail in FIG. 6, is shown aligned with the top of the shoulder 37, and this corresponds with the highest point the clamp bodies 40 and 42 are designed to reach in their path of movement. At this point, the upwardly facing surface of the lip 46 is substantially co-planar with the upwardly facing surface of the shoulder 37. The lip 46 is illustrated having a slight chamfer to avoid jamming during feeding of the component parts, as described below, but this is not required. The lip can be lowered beneath the plate 30 to a lowest point, at which point a tab in the slot 46' can be ejected as described below.

The buffer column 31 is shown in FIG. 5 mounted to the plate 30, with the groove 33 directly below the lower end of the buffer column 31 and above the plate 30. The surface of the buffer column 31 in which the groove 33 is formed is substantially co-planar with the face of the shoulder 37, and this configuration defines the slot 33' therebetween into which the lip 56 is inserted. The lip 56 is preferably the end of the shuttle 50 and is substantially the same thickness as the slot 33', thereby displacing objects in the slot 33' when the shuttle 50 is driven by the ram 52 through the slot 33'.

Figure 17:
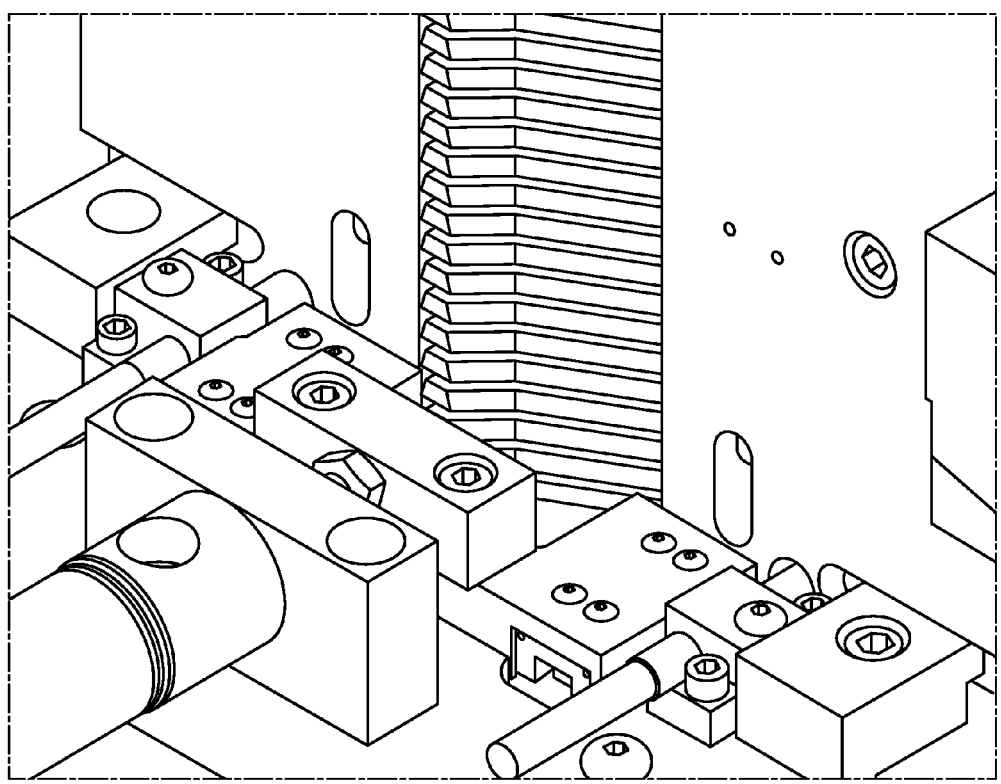
FIG. 17 is a view in perspective illustrating the embodiment of FIG. 1 with a stack of trees installed thereon.

The shuttle 50 is shown in a "dropping" configuration in FIGS. 5 and 6 with the lip 56 displaced out of the slot 33', thereby permitting objects in the grooves 33 and 34 to drop downwardly under the force of gravity. For example, as shown in FIG. 17, there can be a stack of trees in the grooves 33 and 34, and in the dropping configuration the lowest tree 100 drops into the slot 33' and the higher trees rest upon the shuttle 50. The higher trees preferably rest upon the upwardly facing surface 57 of the lip during the dropping configuration.

As viewed in FIG. 7, the ram 52 drives the shuttle 50 toward and away from the buffer columns 31 and 32, thereby displacing the lip 56, and a substantially identical lip 58 through the slots between the buffer columns 31 and 32 and the plate 30. A tree 100 inserted in the space between the buffer columns 31 and 32 is driven by the shuttle 50 as described below, and in relation to FIG. 8 and following.

Figure 8:
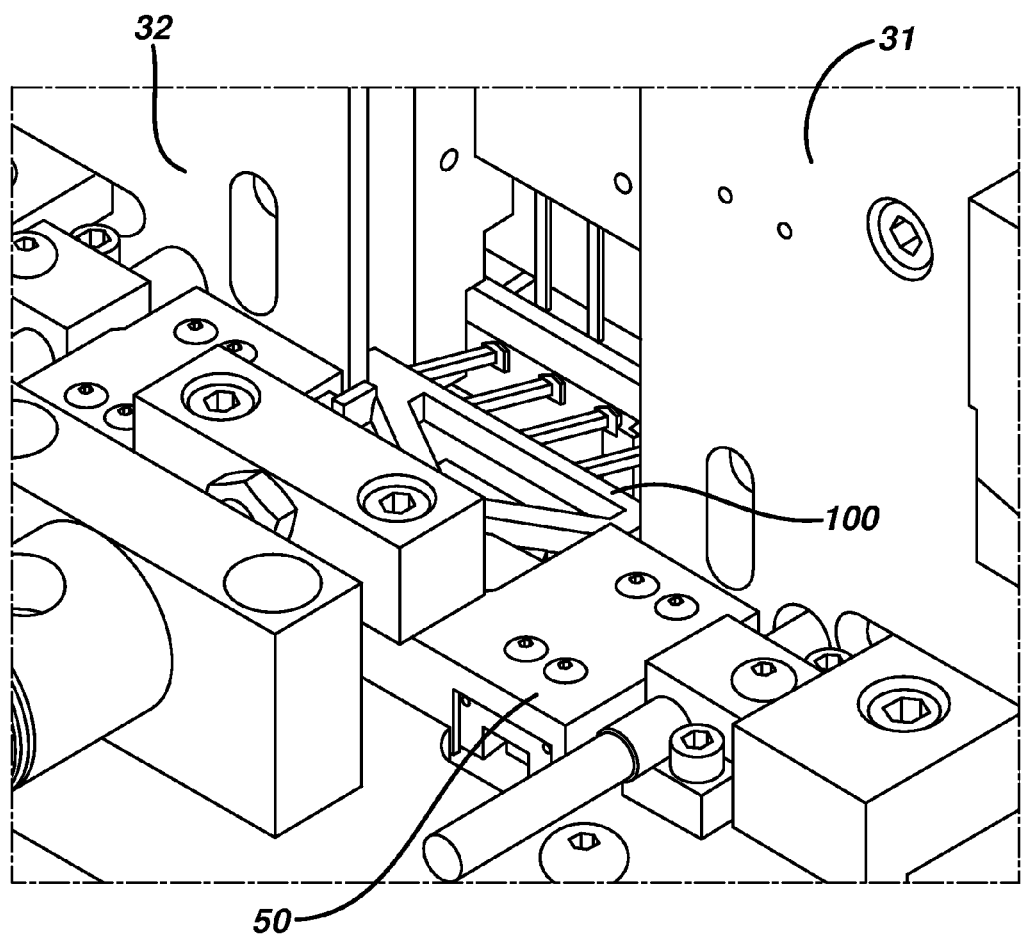
FIG. 8 is a view in perspective illustrating the embodiment of FIG. 1 in a second step of a preferred process.

In FIG. 8, the tree 100 is shown in the space directly between the buffer columns 31 and 32, with its protruding tabs extending laterally into the grooves 33 and 34. The apparatus 10 is in the starting position, in which the tabs of the tree 100 are resting upon the upwardly facing surface 57 of the shuttle. In this position, the tree 100, and any other trees which, in a preferred embodiment, rest upon the tree 100, are above the slot 33' and its corresponding slot on the opposite side of the aperture 32. The surface 57, and a corresponding surface on the opposite side of the aperture, are positioned directly beneath the grooves 33 and 34, thereby preventing any trees from dropping downwardly into the slot 33' and its corresponding slot on the opposite side of the aperture 32.

Figure 9:
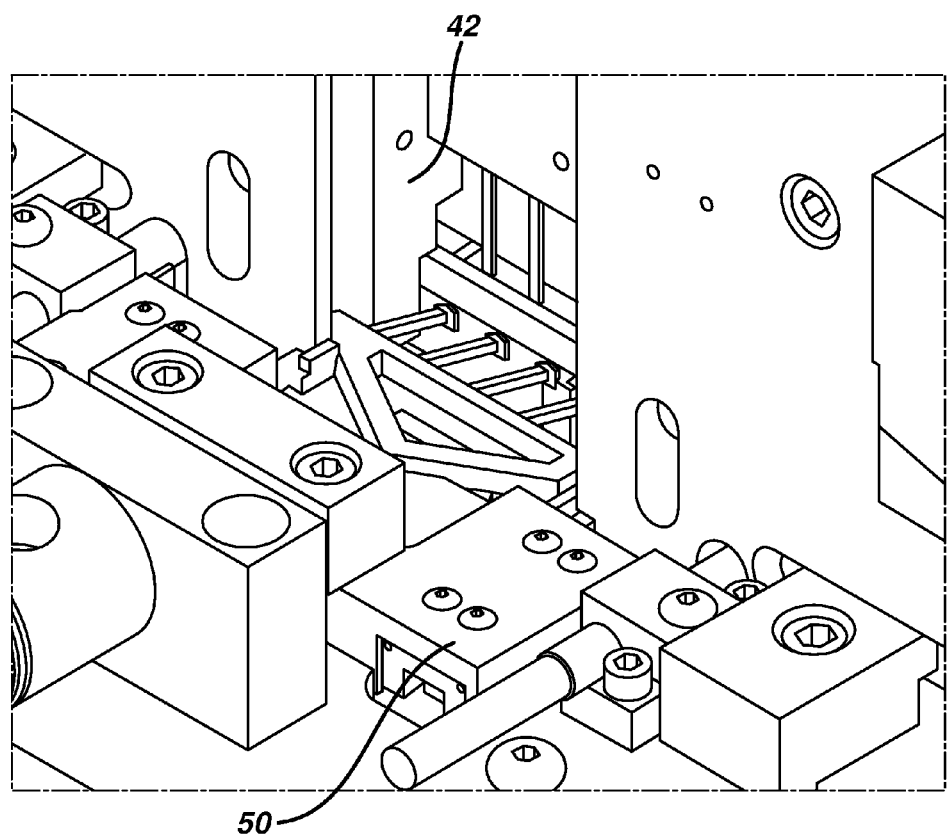
FIG. 9 is a view in perspective illustrating the embodiment of FIG. 1 in a third step of a preferred process.

In FIG. 9, the apparatus 10 is shown in the dropping configuration, shown in FIGS. 5 and 6, after the shuttle 50 has been driven away from the starting position shown in FIG. 8. When the shuttle 50 is pulled to the dropping configuration, the lips in the slots between the lower ends of the buffer columns 31 and 32 and the upwardly facing surface of the plate 30 are moved out of the slots to permit the tabs of the tree 100 to drop downwardly in the grooves 33 and 34. Thus, the tree 100 tabs are positioned in the slots beneath the grooves 33 and 34. When the tree 100 drops, the lower surfaces of the tabs of any trees above the tree 100 preferably remain higher than the lip 56, and preferably higher than the upwardly facing surface 57. In this manner, when the shuttle 50 is driven toward the aperture 32, the lip 56, which is now longitudinally adjacent the tab of the tree 100 (rather than vertically adjacent the tab) is driven into the slot 33' that the tab occupies beneath the next higher tree's tabs.

Figure 10:
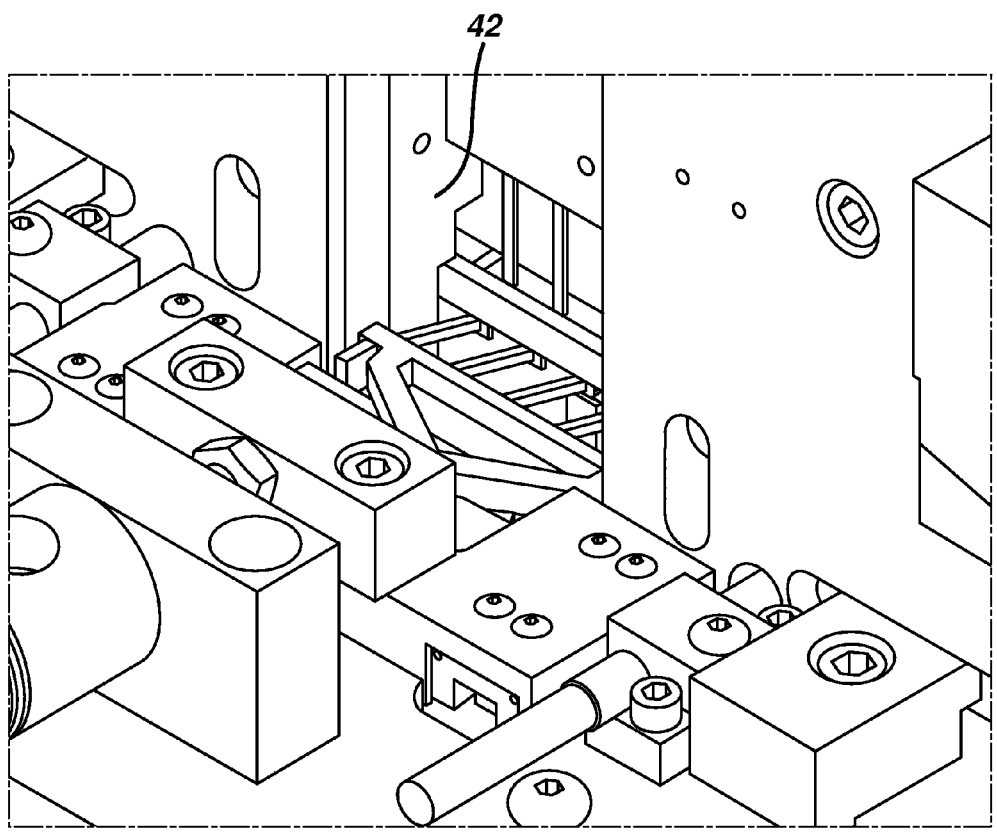
FIG. 10 is a view in perspective illustrating the embodiment of FIG. 1 in a fourth step of a preferred process.
Figure 11:
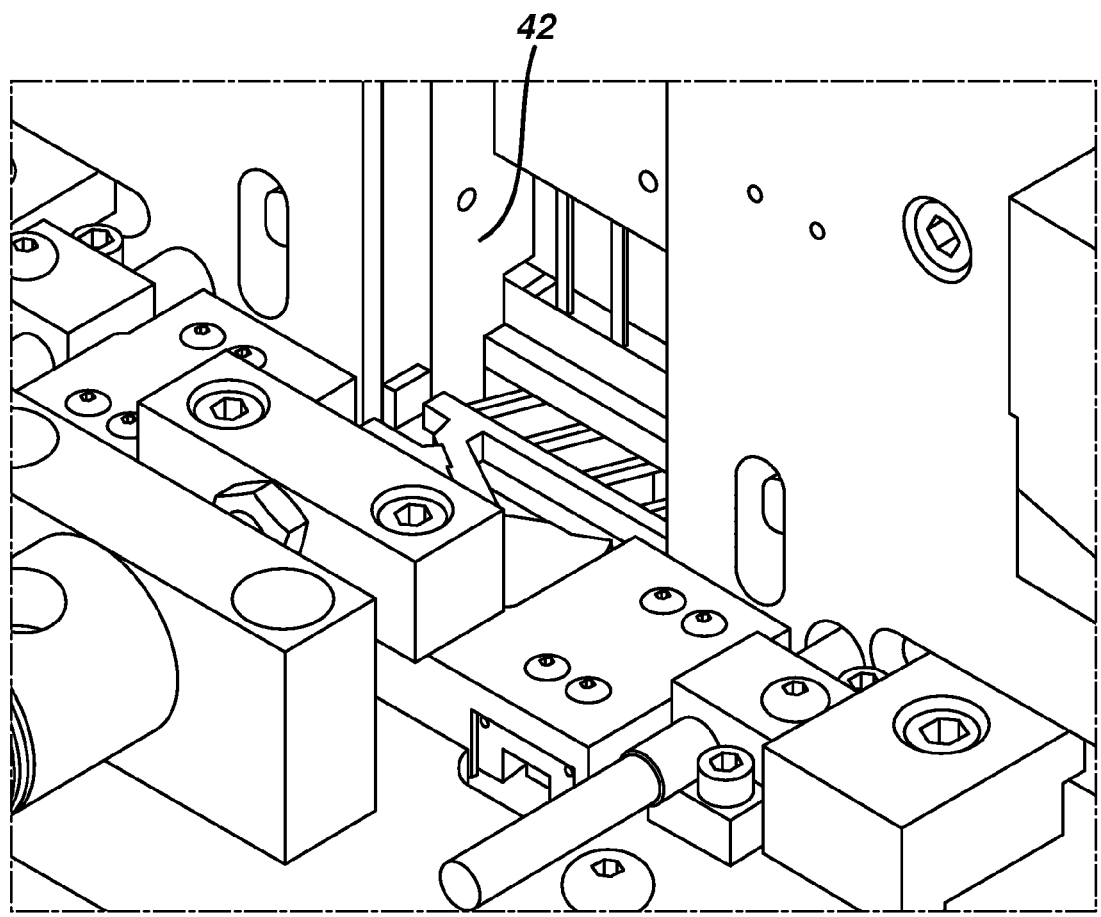
FIG. 11 is a view in perspective illustrating the embodiment of FIG. 1 in a fifth step of a preferred process.
Figure 12:
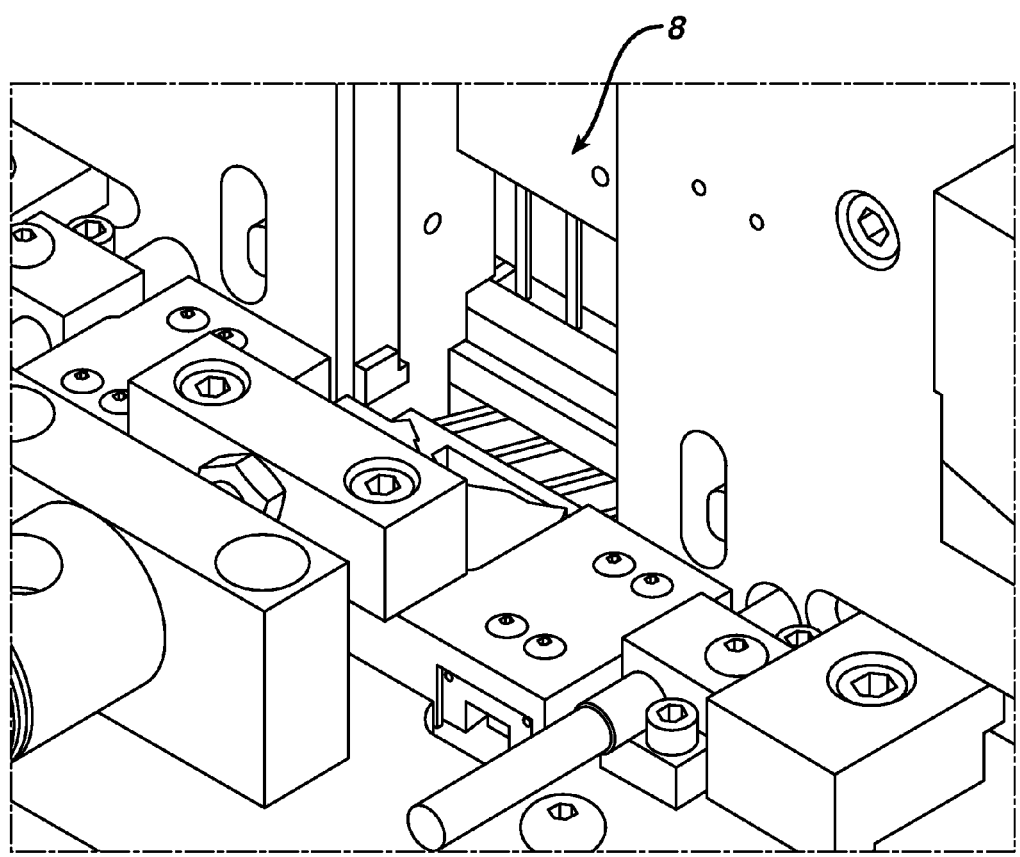
FIG. 12 is a view in perspective illustrating the embodiment of FIG. 1 in a sixth step of a preferred process.

The next step in the process is shown in FIG. 10, in which the tree 100 is driven farther beyond the grooves 33 and 34 so that its tabs extend into the slots 46' and 47' (not shown) above the lips 46 and 47 on the clamp bodies 40 and 42. The tabs of the tree 100 are pushed into the slots 46' and 47' until they are preferably displaced by the shuttle 50 to or near the rear wall of the lips 46 and 47, thereby passing the end of the shoulder 37 and its corresponding shoulder on the opposite side of the aperture 32. The upwardly facing surface 57 occupies the groove 33, thereby preventing any other trees from falling downwardly. In this configuration, the entire tab is beyond the shoulder 37, thereby permitting vertical movement by the clamp bodies 40 and 42 as driven by the rams 36 and 38. This movement is illustrated in FIGS. 11 and 12.

Figure 13:
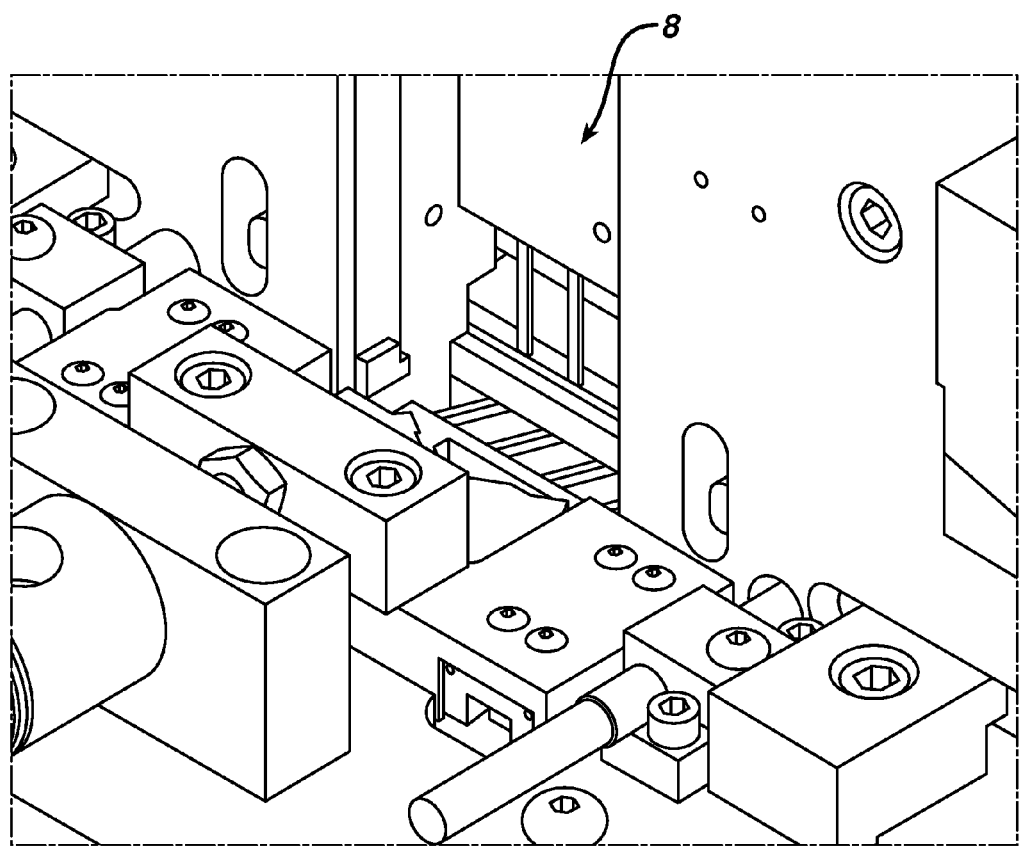
FIG. 13 is a view in perspective illustrating the embodiment of FIG. 1 in a seventh step of a preferred process.
Figure 14:
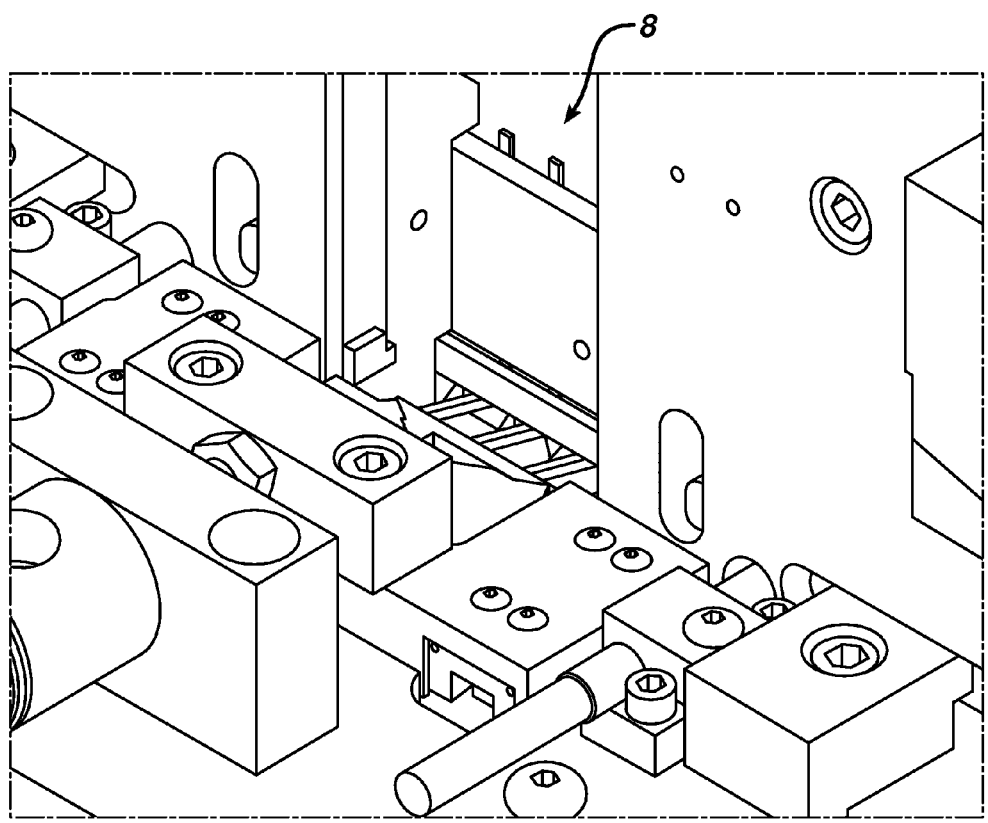
FIG. 14 is a view in perspective illustrating the embodiment of FIG. 1 in an eighth step of a preferred process.
Figure 15:
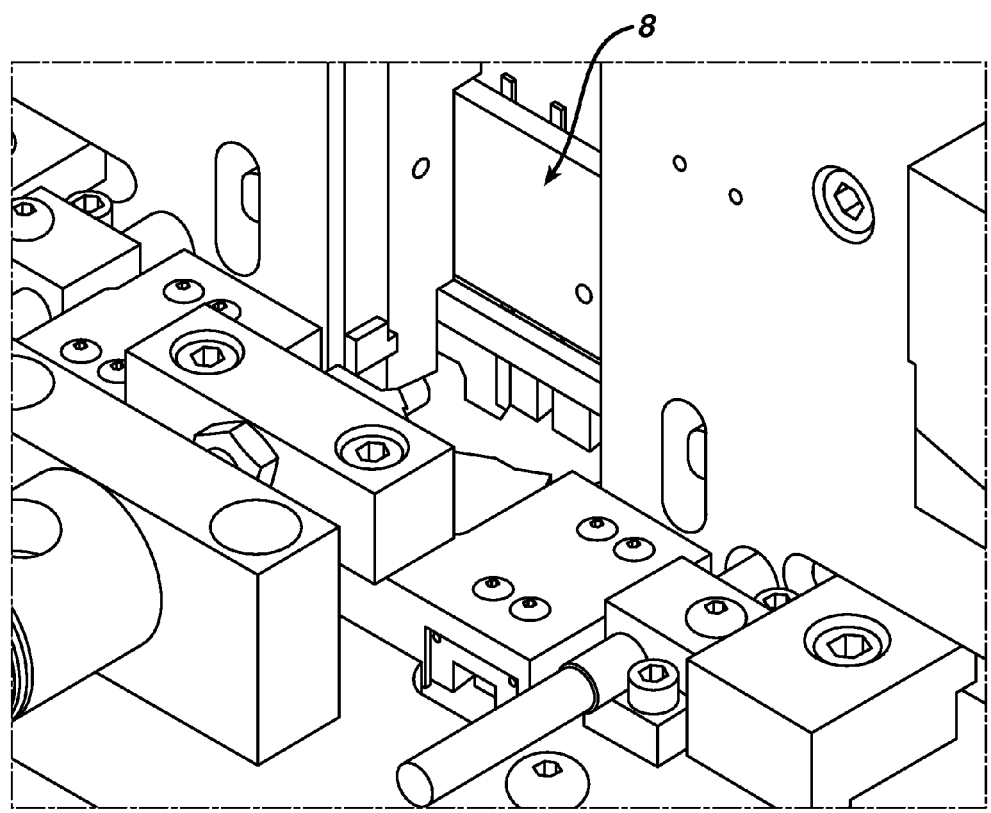
FIG. 15 is a view in perspective illustrating the embodiment of FIG. 1 in a ninth step of a preferred process.
Figure 16:
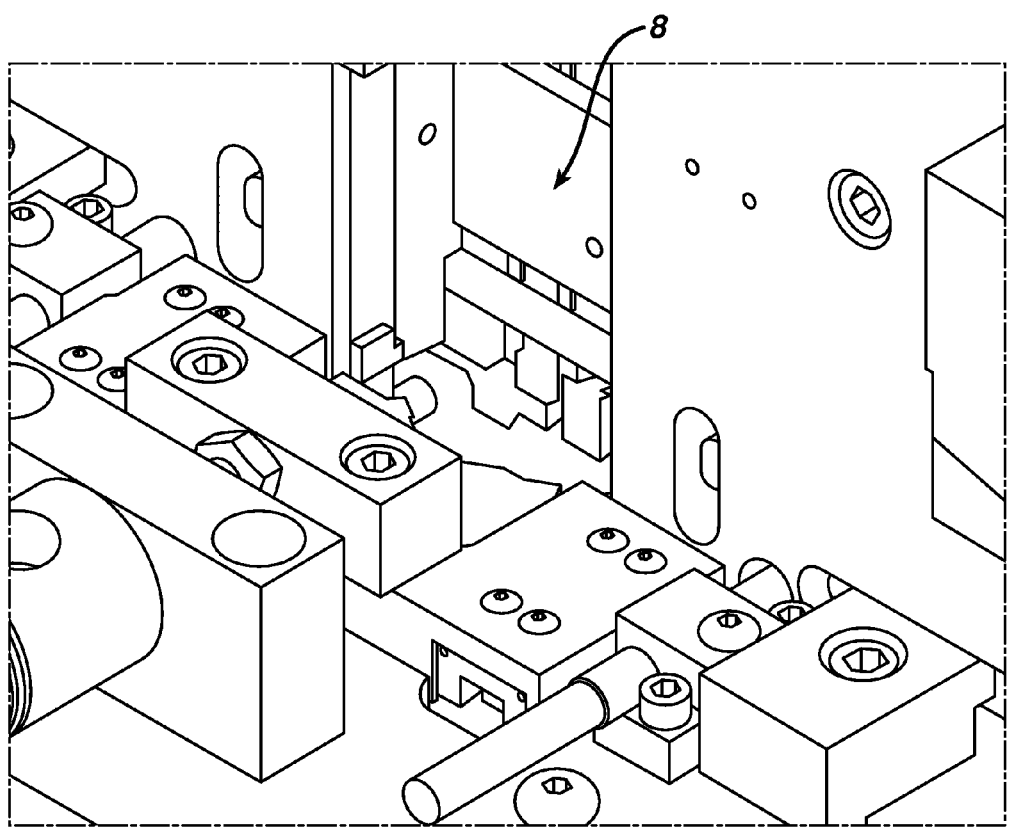
FIG. 16 is a view in perspective illustrating the embodiment of FIG. 1 in a tenth step of a preferred process.

The next step includes movement of the clamp bodies 40 and 42 vertically, at which time the horizontal shuttle 50 is maintained stationary. The vertical movement of the tree 100 forces the drivers into the degating apparatus 8, and proceeds with the clamp bar 44 disposed directly above the branches of the tree 100, thereby clamping the branches against the degating apparatus 8 in order to maintain the drivers thereon in a known position. In FIGS. 13 and 14, the degating apparatus 8 is driven downwardly, thereby removing the drivers from the tree 100 and inserting them in the surgical cartridge. In FIGS.

15 and 16, the degating apparatus 8 is shown reversing its plunging motion, after the scrap from the tree 100 is withdrawn through the apertures 22 and 32. Preferably, an air jet (not shown) blasts air to ensure that the scrap is completely removed.

As shown in FIG. 17, it is contemplated to stack a plurality of trees between the buffer columns 31 and 32, as alluded to above, so that after the lowest tree 100 is driven by the clamp bodies 40 and 42 toward the cartridge and degated, the next lowest tree can be fed toward the cartridge in the same manner. Preferably, a sensor connected to the central computer 16 detects when the stack of trees becomes low enough, according to a predetermined minimum, that a conventional robot (not shown) should be actuated to replenish the supply of trees.

It should be noted that the tree 100 is not the only structure that can be used in association with the invention. Any body that is desirably stacked with the lowest such body in the stack removed and operated upon prior to removal of the next higher body is a candidate for the invention. For example, and without limitation, the invention contemplates a planar blank, a sphere, a cup-shaped object or any other type of body that can be stacked with other like bodies, located by its outer periphery and a lower part in a stack removed from under the next higher part can be disposed in a version of the apparatus 10 that is modified to function according to the principles described above.

It will become apparent that the surface 57 is designed to be as high above the upwardly facing surface of the plate 30 as is needed to ensure that the bottom of the next higher object tab in the grooves 33 and 34 is above the surface 57. If the tab is the highest part of the object, then the surface 57 can be flush with top of the lip 56. If not, the surface 57 must be raised to prevent the next higher object from dropping into the opening under the buffer columns 31 and 32.

It should be noted that it is possible to take more than one workpiece at a time from a stack of workpieces, as long as the structure described above is modified to permit this. For example, it is contemplated that if a plurality of stacked parts can be acted upon, such as by a press or other machine, when the parts are still stacked, an alternative embodiment can drive two or more such stacked parts out of a main stack of many more such parts. Likewise, if the machine that acts upon the plurality of parts can separate the stack, then it is considered equivalent to eject a plurality of stacked parts into the machine rather than a single part, as described in association with the preferred embodiment described above. Still further, it is contemplated that some machines that receive parts from the invention can accept a single part or a plurality of parts. In such a situation, it is contemplated that the number of parts stacked in the apparatus can vary from ejection to ejection. Still further, two stacked parts of a first type have the same height as one part of a second type, the number of parts ejected will vary according to the type of part the apparatus encounters.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. (A method of removing at least one workpiece from a vertical stack of at least two workpieces, the method comprising:
   (a) disposing the stack of workpieces between a first and a second buffer column mounted to a plate;
   (b) driving a shuttle in a first direction to remove a lip of the shuttle from a first slot formed beneath a lower end of at least one of the buffer columns and a top surface of the plate, thereby permitting said at least one workpiece to fall downwardly toward the plate with at least a portion of said at least one workpiece in the first slot;
   (c) driving the shuttle in a second, opposite direction to drive said at least a portion of said at least one workpiece out of the first slot and into a second slot within a clamp body, wherein the second slot is adjacent to and aligned with the first slot; and
   (d) driving the clamp body and said at least one workpiece downwardly.

2. The method in accordance with claim 1, wherein the step of disposing the stack of workpieces between a first and a second buffer column further comprises disposing tabs that protrude from sides of each of the workpieces into complementary, inwardly facing, vertical grooves in the buffer columns.

3. The method in accordance with claim 1, further comprising driving the shuttle in the first direction, after driving the shuttle in the second direction, to permit a second of said at least two workpieces to fall downwardly into the first slot.

4. The method in accordance with claim 1, further comprising disposing additional workpieces to the top of the stack.

5. A method of removing a first workpiece from a vertical stack of workpieces, the method comprising:
   (a) disposing opposing tabs that protrude from opposing sides of each of the workpieces into inwardly-facing vertical grooves in spaced first and second buffer columns mounted to a plate;
   (b) driving a shuttle away from the buffer columns to remove a lip of the shuttle from first slot portions formed beneath lower ends of the buffer columns and a top surface of the plate, thereby permitting the first workpiece to fall downwardly toward the plate, thereby disposing the tabs of the first workpiece into the first slot portions;
   (c) driving the shuttle in an opposite direction toward the buffer columns to drive the first workpiece's tabs out of the first slot portions and into second slot portions within corresponding clamp bodies, wherein the second slot portions are adjacent to and aligned with the first slot portions; and
   (d) driving the clamp bodies and the first workpiece downwardly.

6. The method in accordance with claim 5, further comprising driving the shuttle away from the buffer columns, after driving the shuttle toward the buffer columns, to permit a second workpiece from the vertical stack of workpieces to fall downwardly toward the plate, thereby disposing the tabs of the second workpiece into the first slot portions.

7. The method in accordance with claim 6, further comprising disposing additional workpieces to the top of the stack.

8. An apparatus for retaining a vertical stack of workpieces and removing a first workpiece from the vertical stack and displacing the first workpiece downwardly from the vertical stack, the apparatus comprising:

(a) first and second buffer columns mounted to a plate, the columns having spaced, inwardly-facing, vertical grooves into which opposing tabs protruding from opposing sides of each of the workpieces extend;

(b) first slot portions formed beneath lower ends of the buffer columns and a top surface of the plate;

(c) first and second clamp bodies drivingly linked to at least one prime mover for driving the clamp bodies upwardly to a first position and downwardly to a second position, the clamp bodies having second slot portions adjacent to and aligned with the first slot portions when the clamp bodies are in the first position;

(d) a shuttle slidably mounted in the first slot portions; and (e) a prime mover drivingly linked to the shuttle for driving the shuttle away from the buffer columns to remove a lip of the shuttle from the first slot portions, thereby permitting the first workpiece to fall downwardly toward the plate and disposing the tabs of the first workpiece into the first slot portions, and for driving the shuttle toward the buffer columns to drive the first workpiece's tabs out of the first slot portions and into the second slot portions.

* * * * *